United States Patent [19]

Moore et al.

[11] Patent Number: 5,553,111
[45] Date of Patent: Sep. 3, 1996

[54] APPARATUS AND METHOD FOR IMPROVED TISSUE IMAGING

[75] Inventors: Richard Moore, Concord; Daniel B. Kopans, Waban, both of Mass.

[73] Assignee: The General Hospital Corporation, Boston, Mass.

[21] Appl. No.: 329,295

[22] Filed: Oct. 26, 1994

[51] Int. Cl.$^6$ .................................................. A61B 6/04
[52] U.S. Cl. ............................................ 378/37; 378/208
[58] Field of Search .................... 250/491.1, 363.02; 378/37, 208, 20

[56] References Cited

U.S. PATENT DOCUMENTS

| | | | |
|---|---|---|---|
| 3,971,950 | 7/1976 | Evans et al. | 378/37 |
| 3,974,388 | 8/1976 | Distler et al. | 378/20 |
| 4,131,802 | 12/1978 | Braden et al. | 378/20 |
| 4,696,022 | 9/1987 | Sashin et al. | 378/41 |
| 5,099,503 | 3/1992 | Strömmer | 378/37 |

Primary Examiner—David P. Porta
Assistant Examiner—David Vernon Bruce
Attorney, Agent, or Firm—Choate, Hall & Stewart

[57] ABSTRACT

An improved tissue imaging system is provided, in which tissue can be sheared without direct manual manipulation, so that different perspective images of the tissue can be determined, preferably in a single compression cycle. In one aspect of the invention, a traction system is provided, comprising at least a layer of a radiolucent material dimensioned and constructed such that the layer can pass between tissue and a surface of a tissue imaging device. The radiolucent material has sufficient tensile strength that the layer can slide without tearing against the surface of the tissue imaging device when tension is exerted on the layer, the sliding resulting in movement of the tissue relative to the surface of the tissue imaging device. A method of moving tissue relative to at least one surface of a tissue imaging device is also provided.

32 Claims, 4 Drawing Sheets

REPLACEABLE SHEET

FIG. 4B

APPARATUS AND METHOD FOR IMPROVED TISSUE IMAGING

FIELD OF THE INVENTION

The present invention relates to a system and method for improved tissue imaging, especially for imaging of tissues under compression. In particular, the present invention relates to a mammography system and method for improved imaging of breast tissue.

BACKGROUND

Tissue imaging has proven to be a powerful tool for detection of cancers and other abnormalities within tissues. Mammography, in particular, is an excellent screening technology that has the ability to detect breast cancer several years earlier than physical examination. Early detection results in improved survival and an absolute decrease in mortality from the leading cause of non-preventable cancer deaths in women. The major problems encountered with mammography systems have to do with the difficulty of positioning and retaining breast tissue within the imaging space so that the tissue is thoroughly imaged and the images produced are interpretable.

One problem encountered with standard mammography systems is the difficulty of obtaining different perspective images of the breast tissue that can be effectively compared so that lesions can be identified. In order to detect cancers in breast tissues, mammographers must be able to distinguish malignancies from normal tissue. Breast tissue is composed of glandular tissue (parenchyma), fatty tissue, and supporting connective tissue. When imaged, normal parenchyma can look very much like cancer, and can often only be distinguished from cancer by comparing different perspective images of the breast. Malignancies can also be indicated by clusters of microcalcifications having a particular three-dimensional spatial arrangement that can often only be distinguished from normal clusters of microcalcifications by comparison of different perspective tissue images.

In particular, it is often necessary to compare standard perspectives of the tissue with "rolled" perspectives, in which the tissue is "sheared" (i.e. is deformed by forces tending to produce shearing strain) so that structures that were superimposed on each other in the standard (i.e."non-rolled") perspective are splayed or displaced relative to each other. An analysis of breast cancers missed on mammograms has revealed that the cancers that are most likely to be missed are those that are imaged with superimposed dense glandular tissue (Bird et al., Radiology 184:613–617, 1992).

One of the major problems encountered in mammography, therefore, is that tissue heterogeneity can mimic cancer configurations. There are problems associated with obtaining perspective images that can be easily compared so that malignancies can be identified. In standard mammography systems, "rolled" perspective images are achieved by direct manual manipulation of the breast tissue. A mammography system capable of shearing breast tissue without need for direct manual intervention is needed. A mammography system capable of shearing breast tissue that has already been positioned and imaged in a standard perspective, so that different perspective images of the tissue can be prepared without removing the tissue from the imaging space (and without removing compression, if compression has been applied, see below), would be particularly desirable.

Another problem encountered with standard mammography systems stems from incomplete capture of all relevant tissue within a tissue imaging space. Standard mammography procedures involve compression of the breast against an x-ray detector. The advantages of breast compression include: (i) improved retention of breast tissue for imaging; (ii) higher contrast images with better x-ray penetration and the ability to use lower energy x-rays; (iii) spreading of the internal structures of the breast so that images of the structures can be interpreted; (iv) reduced motion of the breast during imaging; (v) reduced x-ray dose required for imaging of thinner, compressed tissue; (vi) reduced scattering of radiation, resulting in higher contrast images; and (vii) proper positioning of the breast over the detector so that as much tissue as possible can be imaged at one time. In addition, compression forces the breast tissue closer to the detector, thereby improving the geometric sharpness of the image, and also permits uniform exposure over the majority of the breast tissue.

A significant problem encountered with standard compression systems is that compression can actually push tissue out of the field of view. This problem is particularly significant in mammography systems because breast cancers often develop close to the chest wall. Geometrically, the breast wraps around the chest and must be pulled away from the chest in order that x-ray shadows of the inner structures will be projected on the detector and will be recorded. If breast tissues are not held over the recorder, they will not be imaged and cancers will be missed. It is therefore desirable to retain as much tissue as possible within the imaging space, and particularly to be sure that tissue near the chest wall is pulled into, and retained within, the imaging space Previous attempts to solve the problem of extrusion of tissue from mammography systems during compression have included attempts to pull breast tissue into the imaging space by suction. Suction, however, can cause discomfort to the patient. Furthermore, the reduced pressure associated with suction systems may rupture blood vessels and lead to severe bruising.

Other prior art systems designed to limit extrusion from mammography imaging spaces involve compression plates that either are oriented at acute angles (see U.S. Pat. No. 5,029,193 to Saffer), or have associated ridge members along the edge closest to the chest wall (see U.S. Pat. No. 4,962,515 to Kopans).

There remains a need for an improved mammography system capable of pulling breast tissue into the imaging space and/or of spreading or shearing tissue that is disposed in the imaging space.

SUMMARY OF THE INVENTION

The present invention solves the problems associated with positioning and retaining tissue to be imaged within an imaging space, so that tissue analyzed with the improved tissue imaging system of the invention is thoroughly imaged and the images produced are interpretable. The invention provides an improved tissue imaging system in which more tissue is retained in the imaging space and/or in which different perspective images of the tissue can be obtained without direct manual manipulation of the tissue, preferably in a single compression cycle.

In one aspect, the invention provides an improved tissue imaging system in which tissue can be sheared or "translated" without direct manual manipulation, so that different perspective images of the tissue can be determined, preferably in a single compression cycle. In another aspect, the present invention provides a traction system for use in drawing tissue into and retaining tissue within an imaging space, and/or for use in shearing tissue in order to obtain different perspective images of a tissue.

The improved tissue imaging system of the present invention offers several advantages over prior art systems for tissue imaging. For example, the present invention allows tissues to be imaged from a "rolled" perspective, preferably without removal of the tissue from the imaging space and without release and re-compression of the tissue. "Rolled" perspective images can therefore be compared directly to the corresponding standard (i.e. "non-rolled") perspective images to determine if lesions (e.g. malignancies) are present in the tissue.

The traction system of the present invention provides the advantage that it can pull more tissue into a tissue imaging space than can prior art systems. Furthermore, the present traction system can ensure that tissue within a tissue imaging space is spread more effectively. In particular, certain embodiments of the present invention allow tissue to be pulled differentially, depending on its inherent elasticity and/or thickness (i.e. thicker, more elastic tissues would be pulled farther than thinner, more resistant tissues). Such a system will potentially minimize the pain associated with tissue imaging, particularly for imaging systems utilizing tissue compression.

The traction system of the present invention can also provide a disposable contact surface for tissue imaging systems. Contact surfaces (e.g. surfaces that come into contact with a patient's skin) of a tissue imaging system often need to be cleaned thoroughly between patients, particularly since tissues can be damaged when inserted into a localized space (especially when compressed) so that contact surfaces of the imaging system can become soiled with blood or other tissue components. Such cleaning requires expenditure of time and energy. The present traction system can avoid this problem by providing disposable, single-use units that pass between the skin of the subject and contact surfaces of the tissue imaging device.

An additional advantage of the traction system of the present invention is that some embodiments of the system can easily be designed for use with existing tissue imaging devices, such as mammography systems. These embodiments can therefore provide an inexpensive, easy-to-use solution to many of the problems encountered with prior art tissue imaging devices.

The present invention provides an improved tissue imaging device in which tissue to be imaged that is disposed within the device can be sheared without direct manual manipulation of that tissue. The improved tissue imaging device of the present invention comprises a compression plate affixed to a base, a support plate affixed to the base and a means for shearing tissue without direct manual manipulation of that tissue. The compression plate and the support plate are spaced apart from one another, allowing tissue to be positioned therebetween. The shearing means is operationally arranged relative to the plates so that it shears tissue positioned between the plates.

In one embodiment of the improved tissue imaging device of the present invention, either or both of the compression plate and the support plate are capable of lateral translation and/or of twisting relative to one another, so that tissue positioned between the two plates is sheared, and the means for shearing tissue comprises the plate or plates capable of lateral translation and/or of twisting. In another embodiment, a layer of radiolucent material is included that is dimensioned and constructed such that it can pass between surfaces of at least one of the plates of the device and tissue positioned therebetween. The material has sufficient tensile strength that, when tension is exerted on the layer, the layer can slide against the surfaces of the device plates without tearing. In this embodiment, the act of sliding the layer against the surfaces of the plates results in shearing of tissue positioned between the plates, and the means for shearing tissue comprises the layer, The present invention also provides a layer of radiolucent material dimensioned and constructed such that it can pass between tissue disposed within a tissue imaging device and a surface of the device. The material has sufficient tensile strength that, when tension is exerted on the layer, it can slide against the surfaces of the device without tearing. This sliding results in movement of the tissue relative to the surface of the tissue imaging device.

The present invention also provides a traction system for improved tissue imaging comprising i) at least one layer of radiolucent material dimensioned and constructed such that it can pass between tissue disposed within a tissue imaging device and at least one surface of the tissue imaging device; and ii) at least one puller engaged with the at least one layer, for exerting tension on the at least one said layer. The material has sufficient tensile strength that, when tension is exerted on the at least one layer, it can slide against the surfaces of the device without tearing. Tension exerted by the at least one puller on the at least one layer results in sliding of the at least one layer against the at least one surface of the tissue imaging device. This sliding motion results in movement of the tissue relative to the at least one surface of the tissue imaging device.

In preferred embodiments of the traction system of the present invention, the at least one layer comprises a first layer and a second layer, and the traction system is arranged and constructed such that the at least one puller is capable of exerting different tensions on the first layer and said second layer. In particularly preferred embodiments, the traction system of the present invention further comprises an element connecting the first layer and the layer, and the at least one puller is engaged with the first and second layers by means of the connecting element. The first and second layers can be oriented relative to each other such that tension exerted on said first layer can result in tissue movement in a direction different from a direction of tissue movement resulting from tension exerted on said second layer. Also, the first and second layers can be tilted with respect to one another such that the layers are not parallel to one another. In some embodiments of the traction system of the present invention, the at least one puller comprises at least one conveyor drum around which one of the at least one layers passes.

The present invention also provides a compression element for a tissue imaging device comprising a compression plate in operational engagement with at least one layer of radiolucent material, the at least one layer being dimensioned and constructed such that it can pass between tissue and a surface of said compression plate. The material has sufficient tensile strength that the layer can slide without tearing against the surface of the compression plate when tension is exerted on the layer, the act of sliding resulting in movement of the tissue relative to the surface of the compression plate. Preferably, the compression element further comprises a conveyor drum around which one of the at least one layers passes, in operational engagement, to form a conveyor. It is particularly preferred that the compression element further comprise a support plate positioned apart from the compression plate such that the compression plate and the support plate define a compression space therebetween within which tissue can be compressed.

Yet another aspect of the invention provides an imaging detection system comprising a detector apparatus in operational engagement with at least one layer of radiolucent material, the at least one layer being dimensioned and constructed such that it can pass between tissue and a surface of the detector apparatus The material has sufficient tensile strength that, when tension is applied to the layer, it can slide without tearing against the surface of the detector apparatus, the act of sliding resulting in movement of the tissue relative to the surfaces of said detector apparatus. Preferably, the imaging detection system further comprises a conveyor drum around which one of the at least one layers passes, in operational engagement, to form a conveyor. In particularly preferred embodiments of the imaging detection system of the present invention, the detector apparatus comprises a support plate, and the surface of the detector apparatus comprises at least a portion of a surface of the support plate.

The present invention also provides a method of moving a tissue relative to at least one surface of a tissue imaging device comprising the steps of positioning at least one layer of radiolucent material between at least one surface of the tissue and the at least one surface of the tissue imaging device, the radiolucent material being capable of movement relative to the at least one surface of the tissue imaging device; moving the at least one layer of radiolucent material relative to the at least one surface of the tissue imaging device such that at least a portion of the tissue also moves relative to the at least one surface of the tissue imaging device, in the direction of motion of the at least one layer of radiolucent material.

The invention also provides a method of shearing tissue disposed between a compression plate and a support plate of a tissue imaging device comprising laterally translating and/or twisting either or both of the compression plate and the support plate relative to one another.

The invention also provides a mammography device comprising a compression plate and a support plate defining a compression/imaging space therebetween. At least one layer of radiolucent material is dimensioned and constructed such that it can pass between surfaces of either or both of the compression plate and the support plate and surfaces of a breast inserted within the compression/imaging space. The material has sufficient tensile strength that, when tension is exerted on the at least one layer, it can slide without tearing against the surfaces. This act of sliding results in movement of the breast relative to the surfaces least one puller capable of exerting tension on the at least one layer is also included. The mammography device of the present invention is arranged and constructed such that tension exerted by the at least one puller on the at least one layer results in sliding of the at least one layer against the surfaces such that the tissue moves relative to the surfaces.

In preferred embodiments of the mammography device of the present invention, either or both of the compression plate and the support plate are capable of lateral translation and/or of twisting with respect to the other plate, the lateral translation and/or twisting resulting in shearing of tissue disposed within the compression/imaging space between the compression plate and the support plate.

DESCRIPTION OF THE DRAWINGS

Like reference numbers in the Figures refer to like elements.

DETAILED DESCRIPTION OF PREFERRED EMBODIMENTS OF THE INVENTION

The present invention can be implemented on any tissue imaging device in which tissue is confined in a specific space (e.g. in an imaging space). The present invention is particularly valuable for tissue imaging systems that utilize tissue compression, especially for mammography systems.

Figure 1:
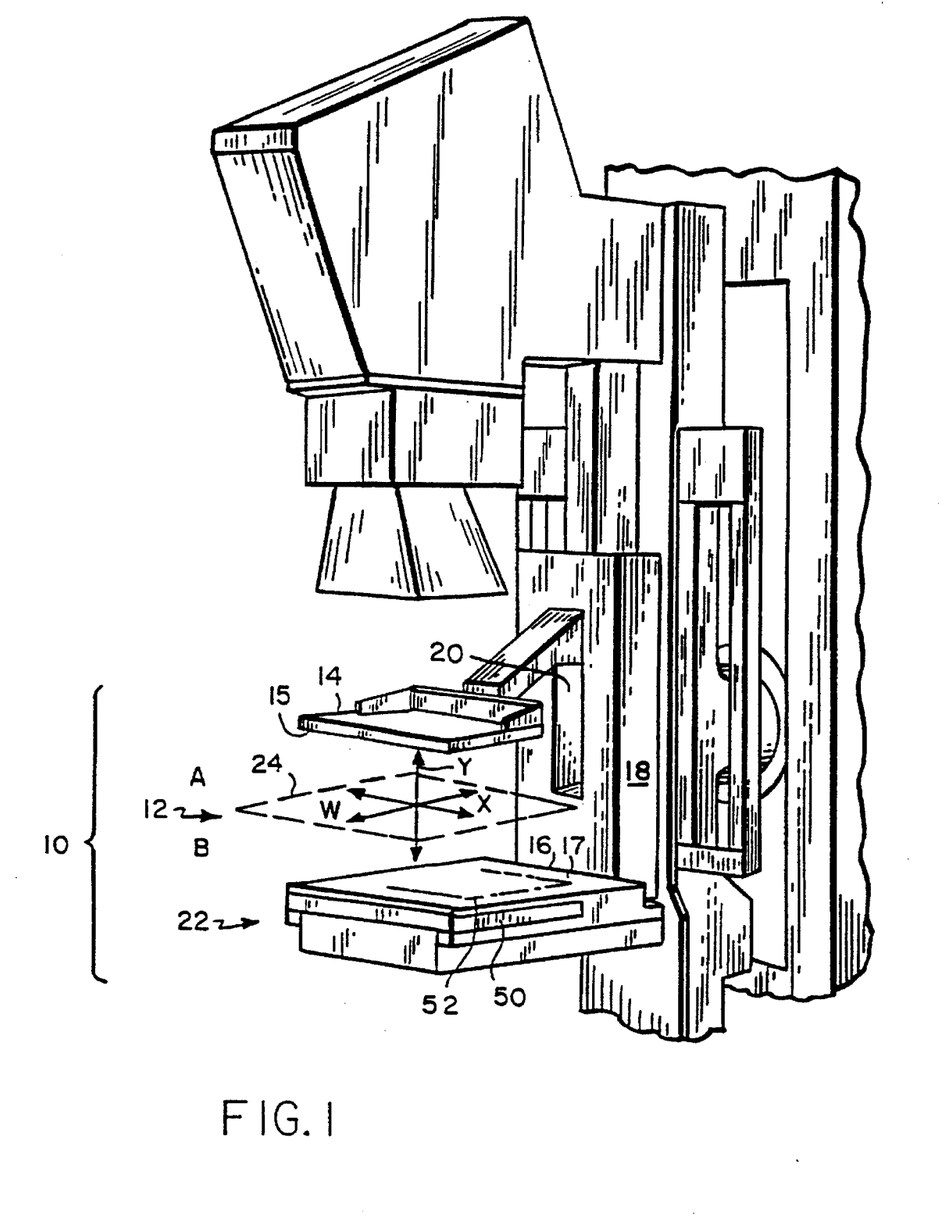
FIG. 1 depicts a standard, prior art mammography system.

Generally, the present invention provides means for pulling tissue into an imaging space, and/or for spreading or "shearing" (i.e. displacing one portion of the tissue with respect to another portion) tissue within that space. FIG. 1 shows a perspective view of a standard mammography system, including a compression system 10. Such standard mammography systems can be obtained from any of a variety of industry sources including, for example, General Electric Corporation, Bennett X-ray Technologies, and Continental X-ray, and, as would be apparent to one of ordinary skill in the art, can readily be adapted to incorporate the improvements of the present invention.

In the standard mammography system depicted in FIG. 1, the boundaries of a compression/imaging space 12 are defined by a compression plate 14 and a support plate 16. As depicted in FIG. 1, each of the plates 14, 16 is attached to a base 18, and the compression plate 14 is slidably mounted in a groove 20 within the base 18. The exact mode of attachment of the plates 14, 16 to the base 18 is not important, except as specified below,and different arrangements are known in the art (see, for example, U.S. Pat. No. 5,029,193 to Saffer; U.S. Pat. No. 3,971,950 to Evans et al.; U.S. Pat. No 4,090,084 to Epstein et al.; U.S. Pat. No. 4,599,738 to Pavetta et al.).

In standard mammography devices such as that depicted in FIG. 1, the support plate 16 is spaced apart from, and typically arranged substantially parallel to, the compression plate 14. In the embodiment depicted in FIG. 1, the support plate 16 overlies and is constructed as part of a detection system 20, comprising a grid 52 and a cassette 50. As is well known in the art, the support plate 18 can alternately be placed at a distance from the detection system 22 (see, for example U.S. Pat. No. 4,599,738 to Paretta et al.). As is also known in the art, the compression plate 14 and the support plate 16 need not necessarily be arranged parallel to one another (see, for example, U.S. Pat. No. 5,029,193 to Saffer). Also, inner surfaces 15 and 17 of the compression plate 14 and the support plate 16, respectively, need not be uniformly flat (i.e. may contain, for example, lips, angled portions, cut-out portions, etc.; see, for example, U.S. Pat. No. 4,962,515 to Kopans, U.S. Pat. No. 3,971,950 to Evans et al.).

FIG. 1 also shows a medial plane 24 and associated coordinate set comprising lateral (X), axial (Y), and transverse (W) axes disposed within the compression/imaging space 12 such that the distance A between the medial plane 24 and the inner surface 15 of the compression plate 14 is substantially the same as the distance B between the medial plane 24 and the inner surface 17 of the support plate 16. It should be understood that the orientation of the medial plane 24 with respect to the rest of the mammography device and/or with respect to the patient is not fixed. For example, as depicted in FIG. 1, the axial (Y) axis is oriented substantially vertically because the compression plate 14 and support plate 16 are substantially parallel to one another and are disposed substantially horizontally. However, other configurations of the compression plate 14 and support plate 16 with respect to one another and with respect to the horizontal are known in the art. Regardless of the orientation or disposition of the compression plate 14 and the support plate 16, the medial plane 24 is disposed substantially equidistantly between them, and defines its associated coordinate system accordingly.

The compression and support plates 14 and 18 of a standard mammography device such as that depicted in FIG. 1 are capable of one or both of two types of motion relative to one another: "axial motion", in which the axial distance (A+B) between the inner surface of the compression plate 14 and the inner surface 17 of the support plate 16 is uniformly varied (that is, A+B is increased or decreased by the same amount for all points on the inner surfaces 15, 17 of the plates 14, 16); and "tilting", in which the axial distance between different points on the inner surface 15 of the compression plate 14 and the inner surface 17 of the support plate 16 is varied differently (that is, A+B is increased or decreased to a different extent at different points on the inner surfaces 15, 17 of the plates 14, 16). For example, for an apparatus in which compression plate 14 and support plate 16 are initially parallel, tilting of one plate 14 or 16 with respect to the other plate 14 or 16 results in loss of parallelism, so that the compression/imaging space 12 defined after tilting has a diverging or converging volume. The term "tilting" is intended to refer to motion that results in formation of a compression/imaging space 12 that converges or diverges along the lateral (X) axis and/or along the transverse (W) axis. As will be apparent to one of ordinary skill in the art, different mammography devices will have different available ranges and directions of tilting motion.

Use of a standard mammography device such as that depicted in FIG. 1 involves inserting a breast into the compression/imaging space 12. Compression can be applied by moving the compression plate 14 and the support plate 16 (in this case along with attendant detection system 22) closer together by axial motion of either or both plates. If desired, the compression plate 14 and support plate 16 can also be tilted with respect to one another during compression. In the standard detection system depicted in FIG. 1, the support plate 16 is fixedly mounted and the compression plate 14 is moveable within a grove 20. With such an apparatus, compression is typically applied by axially moving the compression plate 14 toward the support plate 16. Once the breast (not shown) has been positioned and compressed within the compression/imaging space 12, the breast is imaged by directing a beam of x-radiation (not shown) through the breast and detecting the x-radiation by means of the detection system 22.

Figure 2A:
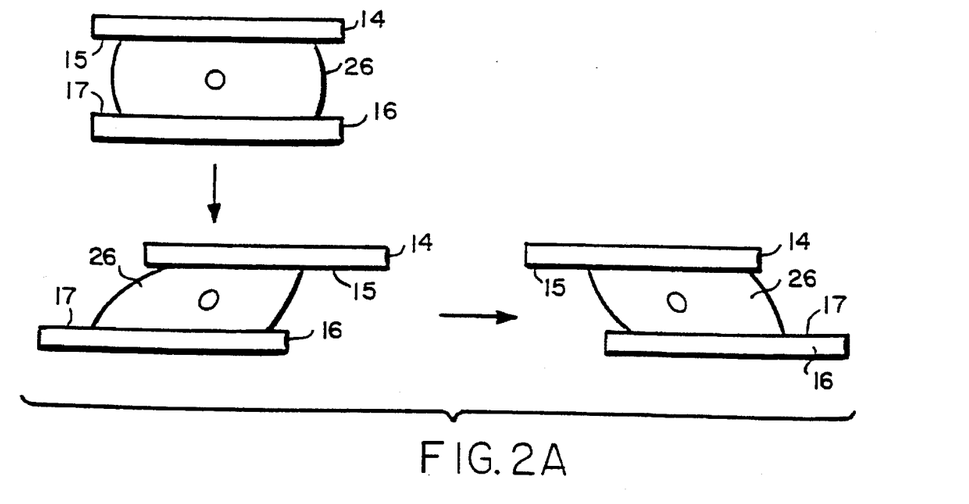
FIG. 2A depicts an end-on view of a compression element of an embodiment of the improved tissue imaging system of the invention, and illustrates the motion herein referred to as "lateral translation".
Figure 2B:
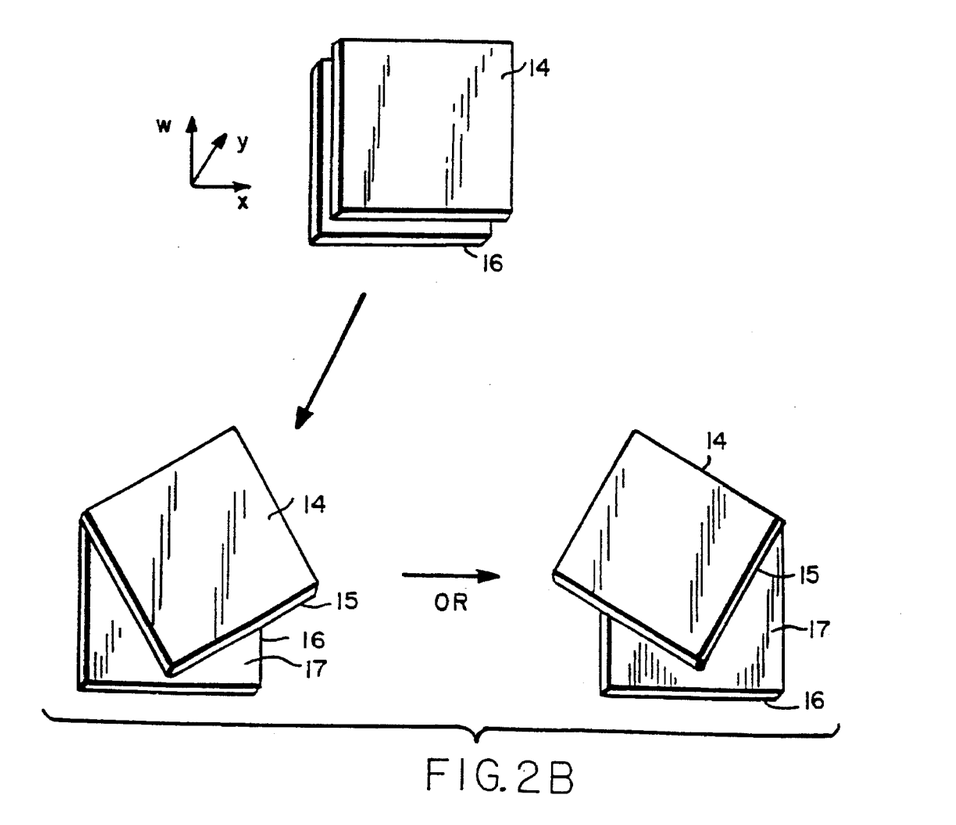
FIG. 2B depicts a top view of a compression element of an embodiment of the improved tissue imaging system of the invention, and illustrates the motion herein referred to as "twisting".

In one aspect of the present invention, an improved tissue imaging system is provided that is capable of shearing tissue within the tissue imaging space. FIG. 2 presents one embodiment of the improved tissue imaging system of the present invention, in which tissue within the tissue imaging space is sheared by motion of one or both of the compression plate 14 and the support plate 16 relative to each other. In the embodiment depicted in FIG. 2, the compression plate 14 and/or the support plate 16 are capable of one or both of "lateral translation" (see FIG. 2A), in which the axial distance (A+B) between the inner surface 15 of the compression plate 14 and the inner surface 17 of the support plate 16 is maintained but the lateral registration between the plates 14 and 16 is varied, and "twisting" (see FIG. 2B), in which either or both of plates 14 and 16 rotate with respect to one another about an axis parallel to or identical with the axial axis (Y) of the medial plane (not shown). That is, areas of plates 14, 16 that were superimposed over each other prior to twisting will no longer be superimposed over each other after twisting. Lateral translation or twisting of one plate 14 or 16 relative to the other plate 16 or 14 results in shearing of tissue disposed between the plates 14 and 16.

To use the improved tissue imaging system having the plate configuration depicted in FIG. 2, one first positions a tissue, preferably a breast 26, between the compression plate 14 and the support plate 16, and applies compression as usual. A standard perspective radiographic image can then be taken of the compressed tissue. In the embodiment depicted in FIG. 2A, the compressed tissue is then sheared by laterally translating either or both of the compression plate 14 and the support plate 16 with respect to one another. In the embodiment depicted in FIG. 2B, the compressed tissue is sheared by twisting either or both of the compression plate 14 and the support plate 16 with respect to one another. Preferably, shearing is performed without first decompressing the tissue. A second radiographic image is then taken, achieving a "rolled" perspective image of the tissue. The two radiographic images can be compared, and triangulations can be performed, using standard imaging processing methods, so that lesions can be distinguished from normal tissue.

Another embodiment of the present invention utilizes a traction system to position and/or shear tissue within a tissue imaging space. The traction system of the present invention comprises a radiolucent material that itself moves within the imaging space and pulls tissue along with it. The material should be sufficiently stiff that it doesn't wrinkle, but sufficiently flexible that it can bend, for example, around corners or wheels, as necessary. The material should also be uniformly radiolucent to the extent that it does not interfere with the passage of imaging radiation through the tissue sample to the detector. We have found that materials such as x-ray film (such as, for example, Kodak miNR film obtainable from Eastman Kodak) work well in the present traction system. Other materials that are likely to be useful in the traction system of the present invention include, for example, polyester, teflon, acetate, polyvinyl chloride, and methyl polyvinyl chloride obtainable from standard industry sources.

The traction system of the present invention may comprise other materials in addition to the radiolucent material described above. These other materials may be, for example, engaged with, attached to, and/or molded with the radiolucent material, so long as the passage of imaging radiation through the tissue to the detector is not detrimentally disrupted.

Figure 3A:
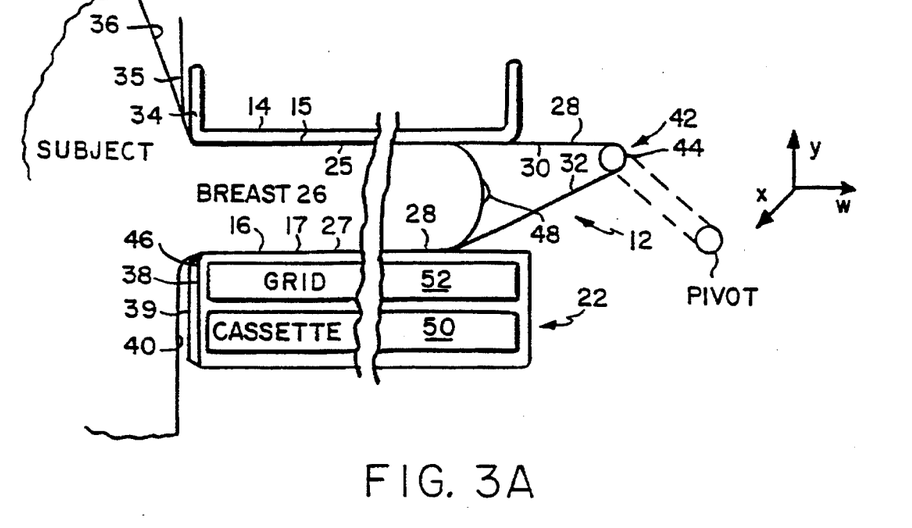
FIG. 3 depicts an embodiment of the traction system of the invention.
Figure 3B:
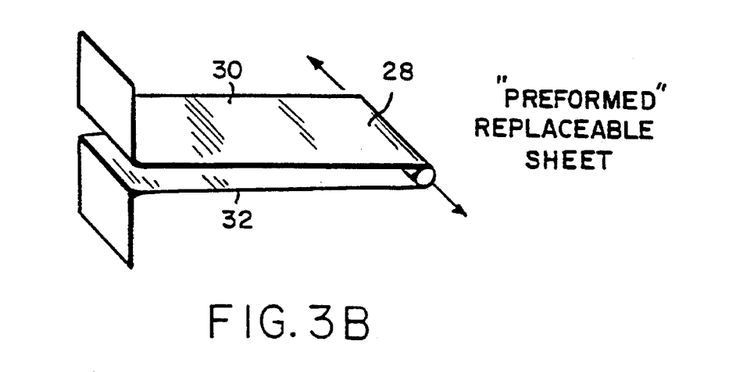

FIG. 3 depicts an embodiment of the traction system of the present invention in use with a standard mammography system. In the embodiment of FIG. 3, radiolucent material 28, shown isolated in FIG. 3b, is formed into a sleeve-like shape with a first layer 30 and a second layer 32, and is arranged around a breast 26. The sleeve of radiolucent material 28 and breast 26 are positioned between the compression plate 14 and the support plate 16. In the embodiment depicted in FIG. 3, the radiolucent material 28 is arranged so that it passes between the subject and surfaces of the tissue imaging device that might otherwise be contacted by the subject's skin.

In particular, the material 28 passes between the inner surface 15 of the compression plate 14 and an upper surface 25 of the breast 26 between the inner surface 17 of the support plate 16 and a lower surface 27 of the breast 26, and also between imaging device surfaces that are external to the compression/imaging space 12 and areas of the subject's body that would otherwise touch those surfaces. Specifically, the radiolucent material 28 passes between a side 34 of the compression plate 14 and an area 36 of the subject's upper rib cage (i.e. above the breast), and also between a side 38 of the detection system 22 and an area 40 of the subject's lower rib cage (i.e. below the breast).

We note that, as presented in FIG. 3, the apparatus is positioned for a "craniocaudal" (CC) projection; the apparatus could alternately be positioned for a "mediolateral oblique" (MLO) projection, in which case the material 28 of the invention would pass between the inner surface 15 of the compression plate 14 and a side of the breast, etc.

The traction system depicted in FIG. 3 includes a pivotable puller 42 that is designed to exert tension on the material 28, and to thereby pull the material toward the puller, in this case away from the subject's body and farther into the compression/imaging space 12. Any available pulling device could be used, such as, for example, a crank, an eccentric, a ratchet, a roller, a hand etc., so long as it is capable of pulling the radiolucent material 28 so that it slides along surfaces of the tissue imaging device. As depicted in FIG. 3, motion of the material 28 pulls breast tissue toward the puller 42, thus pulling the tissue farther into the compression/imaging space 12 and/or spreading out the tissue within that space 12.

As depicted in FIG. 3, the puller 42 is engaged with a connecting element 44 that connects the first 30 and second 32 layers of radiolucent material. It is noted that the puller 42 need not be engaged with such a connecting dement 44, but rather need only be arranged such that it is capable of exerting tension on the layers 30 and 32 to move the radiolucent material 28 relative to surfaces of the tissue imaging device. It is also noted that the connecting dement 44 need not be formed of radiolucent material 26 so long as the passage of imaging radiation through the breast 28 to the detection system 22 is not disrupted.

To use the traction system depicted in FIG. 3 with a standard mammography device, one positions a breast 26 within the sleeve of radiolucent material 28 and within the compression/imaging space 12 of the mammography device. Compression can be applied if desired. Then, tension is exerted by means of the puller 44, on the upper 30 and lower 32 layers of radiolucent material so that the material 28 slides along surfaces of the tissue imaging device, pulling the breast 26 away from the subject's body and in a direction along the axial axis (W) of the medial plane (not shown). The breast 26 is therefore pulled farther into and/or is spread out within the compression/imaging space 12.

Preferably, the puller 44 is designed to pivot so that the first layer 30 and the second layer 32 of the radiolucent material 28 are not necessarily pulled the same distance, but rather are pulled to the same final tension. Such an arrangement is desirable because, typically, not all areas of the breast 26 are equally flexible. In particular, especially after compression, the upper surface 25 of the breast 26 is typically more taut than is the lower surface 27. The bottom of the breast 26 can therefore be pulled farther without discomfort. On the other hand, tissues 44 immediately under the breast 26 are often particularly delicate and susceptible to tearing. It is therefore desirable to be able to adjust the tension applied to different areas of the breast 26 to maximize spreading but minimize damage.

One side effect of differential pulling is that the nipple 48 of the breast 26 may not always be in profile after the breast 26 has been pulled by the traction system of the present invention. Although mammographers have historically preferred to take images in which the nipple is in profile, we have not found any significant benefit to such an arrangement and believe that the value of fully spread tissues is more significant than the primarily aesthetic advantages conferred by symmetric nipple positioning.

Once the breast 26 has been pulled into and/or spread within the compression/imaging space 26, the breast 26 is imaged as described above.

As mentioned above, the radiolucent material 28 depicted in FIG. 3 is arranged and constructed so that it passes between the subject and surfaces of the tissue imaging device that might otherwise be contacted by the subject's skin. While it is not necessary that the material 28 pass between all potentially touching surfaces, avoiding contact between skin and the imaging device can provide certain advantages including, for example, (i) the subject's skin is not irritated by contact with the device (and particularly is protected from sliding against the surfaces of the device); and (ii) the material 28 provides a disposable surface intervening between the device and the subject, with attendant sanitary advantages.

Thus, the sleeve of radiolucent material 28 depicted in FIG. 3 is preferably dimensioned to avoid contact between the subject's skin and the surfaces of the imaging device. Motion of the radiolucent material 28 away from the subject's body will effectively shorten those portions 35 and 39 of the material passing between the subject's body and the imaging device surfaces that are external to the compression/imaging space 12 (e.g. between the area 36 of the upper rib cage and the side 34 of the compression plate, and between the area 40 of the lower rib cage and the side 38 of the detection system). Portions 35 and 39 of the material 28 should therefore desirably be sized so that, after the material 28 has moved relative to surfaces of the imaging device, material 28 will still pass between the subject's body and the external imaging device surfaces (e.g. sides 34 and 38). On the other hand, portions 35 and 39 of the radiolucent material 28 should not be so long that they interfere with the imaging process. In particular, it is desirable to avoid bending of portion 35 across the path of imaging radiation. Such bending could be avoided, for example, by shortening portion 35 and/or by providing an additional support (not shown) that prevents portion 35 from interfering with the imaging radiation.

The radiolucent material 28 depicted in FIG. 3 is preferably dimensioned to fit in a compression/imaging space 12 of a mammography device. In particular, it is desirable that the radiolucent material 28 not be significantly wider than is the detection system 22. In the embodiment depicted in FIG. 3, the detection system includes a film-screen cassette 50 that is part of the detection system 22. In this embodiment, it is desirable that the radiolucent material 10 not be significantly wider than is the film-screen cassette 50. Typical film-screen cassettes, such as those available from Eastman Kodak, Agfa, Dupont, or other industry sources, are 18 or 24 cm wide and 24 or 30 cm long. The radiolucent material 28, then, is preferably also approximately 18 or 24 cm wide and is preferably long enough that it can fold over the breast 26 within the compression/imaging space 12, as shown, and also can pass between the subject's upper-rib-cage area 36 and the side 34 of the compression plate 14, and between the subject's lower-rib-cage area 40 and the side 38 of the detection system 22 after having been pulled.

The radiolucent material 28 can also be dimensioned to fit within a groove (not shown) on the support plate 16 and/or on the compression plate 14 so that edges of the material 28 are not exposed and thus will not abrade the subject whose tissue is being imaged.

Although FIG. 3 depicts the radiolucent material 28 folded over the breast 26 in a sleeve-like configuration, alternate configurations of the material 28 can be used in the traction system of the present invention. For example, the material 28 may be configured to encompass the breast 26 on all sides in a tubular arrangement. It is not necessary that a single piece of radiolucent material 28 be used in the traction system of the present invention. For example, two (or more) separate layers of radiolucent material 28 could be used, each of which passes along a different portion of breast surface and each of which is engaged with either its own puller, or with the same puller. In some cases, it may be desirable to have radiolucent material 28 only on one breast surface, or on only a portion of one breast surface (for example, to pull only a particular segment of breast tissue). Under such circumstances, however, it will be important to ensure that edges of the material 10 do not damage tissue adjacent to the portion being pulled.

It may be desirable to construct the traction system of the invention so that differential tension can be applied across a single surface of the breast 26. This can be accomplished in any of a variety of ways including, utilizing a variably hardened elastomer as the radiolucent material or, as mentioned above, utilizing a strip of radiolucent material 26 that only pulls one portion of a breast surface. For example, it may be useful to utilize a strip of material 26 passing down the center of the lower surface 27 of the breast 26, where tissue is often particularly thick.

Alternately, in the case mentioned above where multiple strips of material 28 are utilized, with differential tensions can be applied to each strip, such that different portions of the breast tissue are pulled to different extents. Or, more preferably, single layers of material 28 that have inherent variable elasticity could be utilized. For example, layers of variable thickness will tend to be more elastic (i.e. will stretch more) where they are thinner and less elastic (i.e. will stretch less) where they are thicker. Engagement of such a variably-elastic layer with a puller (or pullers) results in variable movement of different regions of the layer (e.g. less elastic portions move farther), and therefore variable movement of the tissue below. A traction system utilizing such variable-elasticity layers will pull more flexible tissues (for example, thicker tissues) are farther than less flexible tissues, and will therefore minimize damage to the tissue and will also minimize pain.

It is also not necessary that the direction of movement of the radiolucent material 28, and therefore of the breast 26, be away from the subject's body and/or substantially parallel to the transverse axis (W) of the medial plane 24. In some instances, for example, it may be desirable to spread breast tissue laterally, along the lateral axis (X) of the medial plane 24, and therefore to arrange the traction system so that the radiolucent material 10 moves laterally across the compression/imaging space 12 (i.e. into or out-of the page with respect to FIG. 3). Such an arrangement could also be useful to shear the breast for "rolled" images that can be compared to "non-rolled" images as to determine the presence of malignancies.

Figure 4A:
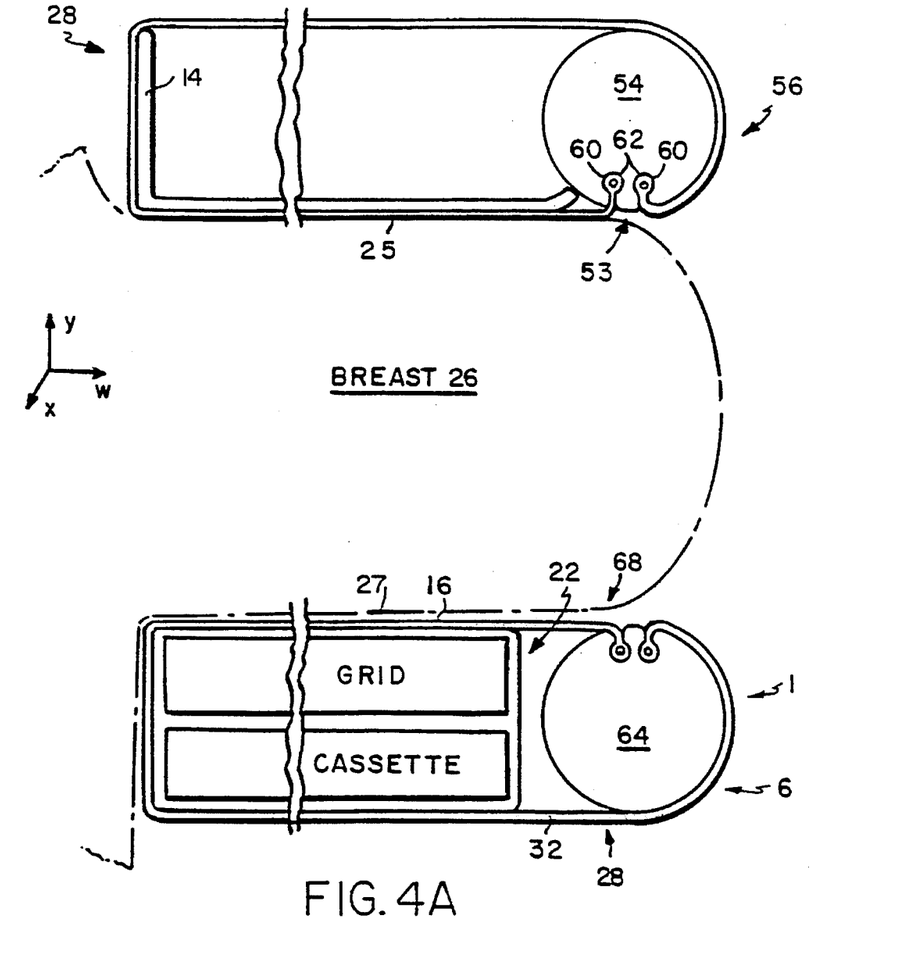
FIG. 4 depict a second embodiment of the traction system of the invention.
Figure 4B:
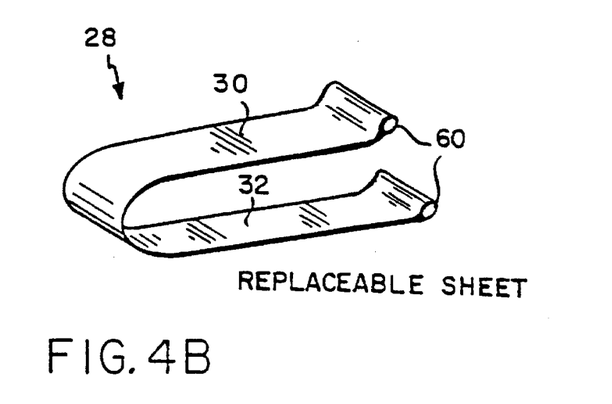

FIG. 4 shows an alternate embodiment of the traction system of the present invention, incorporated as part of a compression/imaging system in a mammography device. In the embodiment of FIG. 4, a first layer 30 of radiolucent material 28 is arranged around a first drum 54 as part of a first conveyor 56. The first layer 30 is engaged with the first drum 54 by means of any convenient attachment element 58. As depicted in FIG. 4, the attachment element 58 comprises attachment members 60 on the radiolucent material 28 that are matingly engaged with indentations 62 in the first drum 54. Any other attachment element may be utilized, including, for example, a clamp, adhesive, hook-and-loop fastener (e.g. VELCRO™), or suction (i.e. vacuum).

For ease of construction, the attachment members 60 depicted in FIG. 4 comprise loops of radiolucent material 28. The attachment members 60 may alternately comprise any material that can be inserted in the first drum indentations 62 so that the first layer 30 of radiolucent material and first drum 54 are operationally engaged with one another as a first conveyor 56.

In the embodiment of FIG. 4, the first layer 30 also wraps around the compression plate 14. A second layer 32 of radiolucent material 28 passes around a second drum 64 and also around a support plate 16 that is integral with a detection system 22, as part of a second conveyor 66. The second layer of radiolucent material is engaged with the second drum by means of a second attachment element 68. There is a significant advantage of the arrangement depicted in FIG. 4 specifically, by having separate conveyors 56 and 66 moving the radiolucent material 28, the different layers 30 and 32 of radiolucent material 28 can be moved to different extents, depending, for example, on the flexibility of the tissue they are pulling.

The first 56 and second 66 conveyors depicted in FIG. 4 can also be oriented relative to one another so that the first 30 and second 32 layers of radiolucent material 10 are not necessarily moved in the same direction. For example, the first conveyor 56 may be oriented with respect to the second conveyor 66 so that the upper surface 25 of the breast 26 is moved in a direction substantially perpendicular to a direction that the lower surface 27 of the breast 26 is moved. Such an arrangement allows breast tissue to be pulled in different directions and particularly allows "rolled" images to be obtained with ease. Ideally, both "rolled" and "non-rolled" images will be obtainable during the same compression cycle, by rotating at least one of the conveyors 56 and 66 relative to the other, thereby saving time and also minimizing stress to the subject.

The conveyors 56 and 66 depicted in FIG. 4 also need not be arranged parallel to one another. It might be desirable to orient the components of a mammography compression device (e.g. in this case the first conveyor 56, which includes the compression plate 14, and the second conveyor 66, which includes the support plate 16) so that they are tilted toward each other and the compression/imaging space 12 has a volume that converges toward the nipple-end of the breast 26. While this arrangement has advantages in that thinner tissue can be flattened more effectively, a major disadvantage is that even more tissue is extruded from the compression/imaging space 12 under these circumstances.

The traction system of the present invention can overcome this disadvantage by pulling breast tissue farther into the compression/imaging space 12, so that the breast 26 can be fully imaged when the first conveyor 56 and the second conveyor 66, along with its attendant detection system 22, are tilted with respect to one another.

To use the traction system depicted in FIG. 4, one positions a breast 12 between the first conveyor 56 and the second conveyor 66. The breast 26 can be compressed by moving either or both of the first conveyor 56 and second conveyor 66 so that the distance between the two conveyors 56 and 66 is reduced. Then, either or both of the first conveyor 56 and the second conveyor 66 is activated so that the first layer 30 and/or the second layer 32 of radiolucent material moves and breast tissue is pulled in the direction of movement. For example, both conveyors 56 and 66 may first be activated so that the layers 30 and 32 of radiolucent material 28 both move in a direction away from the subject's body and substantially parallel to the long axis of the compression/imaging space 12. Then, one of the conveyors (e.g. the first conveyor 56) can be pivoted with respect to the other conveyor (e.g. the second conveyor 66) so that, when the first conveyor 56 is activated, the first layer 30 moves in a direction substantially perpendicular to it's previous direction of movement and pulls breast tissue substantially laterally.

EXAMPLE

Further aspects and advantages of the present invention are pointed out in the following example. However, it should be noted that this example is merely illustrative of the present invention and is not intended to be limiting.

EXAMPLE 1

Comparison of an improved mammographic system utilizing a traction system of the invention with standard mammographic systems.
GENERAL APPROACH:

An improved tissue compression and imaging device that utilizes a traction system of the present invention is provided by modification of an existing device (General Electric DMR). The modifications do not affect patient safety. Compression force in the improved device is controlled by the same method as used on the standard clinical system: the breast is compressed by a motor driven system to a preset level of compression force and additional tension is applied through a manual system before the mammogram is obtained The improved tissue compression and imaging device of the present invention has the following advantages over standard devices:

1) The new tissue compression and imaging device can improve breast compression and image quality.
2) The new device allows equal or greater volume of breast tissue to be imaged.
3) Patient radiation dose is equal or less than with standard compression systems.
4) The proposed system does not result in any increase in patient discomfort.

PROTOCOL:
Obtaining the mammograms:
Mammograms obtained with a conventional compression system are compared with those obtained using the improved device of the present invention on 30 randomly-selected women who are at least 40 years of age and who are not pregnant. The typical procedure for screening mammograms is to obtain two mammograms for each breast. A craniocaudal (CC) projection and a mediolateral oblique (MLO) projection are obtained for each breast using the conventional compression system. Two additional CC and two additional MLO projections are obtained on a breast using the inventive device. Therefore, four additional views are obtained for each breast. Images are obtained both before and after traction, in order that a valid comparison of image quality can be made.

Data recording:

The mammography devices print out a label for each film obtained, which label includes the compressed breast thickness, kilovoltage, date, time, projection and the milliampere seconds (mAs). The mAs, kVp, and compressed breast thickness may be used to calculate the mean glandular radiation dose. In addition, the tension of the system used for each film is recorded by a technologist. The patient's age and weight are also recorded. The technologist also inquires as to the relative discomfort of the conventional and improved compression system, and records the answers (increase, decrease or approximately the same).

Comparison of compression methods:

The comparison of films obtained with the two compression systems is based on scoring of the images by three radiologists experienced in mammography. The matched pairs of images from the same breast are placed on a viewbox and each radiologist score the overall image quality, compression, and the visibility of structures in different regions of the breast. Physical measures of the images will include regional film density, loss or gain in the amount of breast tissue imaged near the chest wall and breast image area (as an indicator of compression, since increased compression will result in the breast image area increasing).

Interpretation of Data:

Scoring of the clinical image quality utilizes a 4 point scale (1=suboptimal, 2=satisfactory, 3=good, 4=excellent). The three radiologists are encouraged to use intermediate grades to indicate subtle differences between image paris. A paired T-test is used to test for significance. There are a total of 30 CC views and 30 MLO views obtained with each compression system. Significance is tested for each reader and for each question. Image comparison is performed using a known method, previously utilized in a study of chest radiography (Niklason et at., Radiology 186:387–393, 1993). Previous results indicate that a difference in the mean score of 0.3 between two methods is sufficient to demonstrate significance at the $p = 0.05$ confidence level. Thirty comparisons in two views are obtained to permit detection of a consistent difference. In addition, a sample size of 30 women should be large enough to average out spurious effects due to the wide range of breast thickness, size and radiographic density of breasts in a random sampling of women. It is likely that the improvement in image quality will be more significant on radiographically dense breast images. All of the images are scored in one reading, under typical film viewing conditions. These viewing conditions include the use of high luminance mammography viewboxes, masking of light around the edges of the film, and no room lights. There will be no time limit on the film reading.

RISKS:

The mean glandular radiation dose for a typical mammography image on the conventional unit that will be used is 115 mrads (average size breast). The radiation dose per film with the improved device will be similar to that from a conventional compression system. To convert to effective "whole body equivalent" dose we use a tissue weighing factor of 0.1 (we use a tissue weighing factor of 0.1 rather than the tissue weighing factor of 0.05 suggested for the general population because all of the subjects are women). Therefore, the effective dose is 115 mrads ×0.1=11.5 mrads. This is approximately the same effective dose as a chest exam and may be compared to an annual background radiation exposure of 300 mrads per image. The four additional exposures will result in an additional radiation dose equal to 8% of natural background. The risk from this radiation dose is minimal.

There is also a risk of increased discomfort with the improved compression system of the present invention. The discomfort of reimaging a breast in two views is comparable to the discomfort experienced for each breast in the standard procedure, except that the intraction exposure is done immediately after the pre-traction exposure without releasing compression. This lengthens the compressed time by about 60 seconds. We have compressed the breasts of several volunteers and, although they have reported a feeling of increased compression, no increase in discomfort was reported. This may be due to the fact that the increased compression with the new system is mostly in areas which were previously under low compression. The compression force used can be modified if an increase in discomfort is observed.

BENEFITS:

Increased breast visualization will improve the detectability of tumors residing centrally toward the chest wall and deep axillary regions. Additional views might also be avoided, through consistent complete visualization. Improved ergonomics will decrease positioning time and required skill level, thereby decreasing study time and improving comfort and data integrity (completeness).

Equivalents

It should be understood that the preceding is merely a detailed description of certain preferred embodiments of the present invention, and that the scope of the invention is not meant to be limited by this description. It will be apparent to one of ordinary skill in the art of tissue imaging that various modifications and equivalents of the embodiments herein described can be made without departing from the spirit or scope of the invention.

What is claimed is:

1. An improved tissue imaging device comprising:

a compression plate affixed to a base;

a support plate affixed to said base and spaced apart from said compression plate for positioning tissue to be imaged therebetween; and means for shearing tissue operationally arranged relative to said plates such that said means for shearing tissue is capable of shearing tissue disposed therebetween plates without direct manipulation of said tissue.

2. The improved tissue imaging device of claim 1 wherein either or both of said compression plate and said support plate are capable of lateral translation relative to each other, so that tissue positioned between said compression plate and said support plate is sheared and said means for shearing tissue comprises said plate or plates capable of lateral translation.

3. The improved tissue imaging device of claim 1 wherein either or both of said compression plate and said support plate are capable of twisting relative to each other, so that tissue positioned between said compression plate and said support plate is sheared and said means for shearing tissue comprises said plate or plates capable of twisting.

4. The improved tissue imaging device of claim 1, wherein said means for shearing tissue comprises a layer of radiolucent material dimensioned and constructed such that said layer can pass between surfaces of at least one said plate and tissue positioned therebetween, said material having sufficient tensile strength that said layer can slide without tearing against said surfaces when tension is exerted on said layer, said improved tissue imaging device being arranged and constructed such that sliding said layer against said surfaces results in shearing of tissue positioned between said plates.

5. An imaging device comprising:

a compression plate and a support plate defining a compression/imaging space therebetween;

at least one layer of radiolucent material dimensioned and constructed such that said at least one layer can pass between surfaces of either or both of said compression plate and said support plate and a tissue inserted within said compression/imaging space, said material having sufficient tensile strength that said at least one layer can slide without tearing against said surfaces when tension is exerted on said layer, and at least one puller capable of exerting tension on said at least one layer so as to slide said at least one layer against said surfaces such that said tissue moves relative to said surfaces so as to effect at least one of (a) pulling the tissue into the imaging device without substantially moving other portions of a patient's body to which the tissue is attached, and (b) shearing of the tissue.

6. A traction system for improved tissue imaging comprising:

at least one layer of radiolucent material dimensioned and constructed such that said layer can pass between tissue disposed within a tissue imaging device and at least one surface of said tissue imaging device, said material having sufficient tensile strength that said at least one layer can slide without tearing against said at least one surface of said tissue imaging device when tension is exerted on said at least one layer, said sliding resulting in movement of at least a portion of said tissue relative to said at least one surface of said tissue imaging device; and at least one puller engaged with said at least one layer, said at least one puller for exerting tension on said at least one said layer, said traction system being arranged and constructed such that tension exerted by said at least one puller on said at least one layer results in sliding of said at least one layer against said at least one surface of said tissue imaging device such that said tissue moves relative to said surface of said tissue imaging device so as to effect at least one of (a) pulling the tissue into the imaging device without substantially moving other portions of a patient's body to which the tissue is attached, and (b) shearing of the tissue.

7. The traction system of claim 6 wherein said at least one layer comprises a first layer and a second layer, said traction system being arranged and constructed such that said at least one puller is capable of exerting different tensions on said first layer and said second layer.

8. The traction system of claim 7, further comprising an element connecting said first layer and said second layer, said at least one puller engaged with said first and second layers by way of said connecting element.

9. The traction system of claim 7, wherein said first layer and said second layer are oriented relative to each other such that tension exerted on said first layer can result in tissue movement in a direction different from a direction of tissue movement resulting from tension exerted on said second layer.

10. The traction system of claim 7 or claim 9, said first layer and said second layer being tilted with respect to one another such that said layers are not parallel to one another.

11. The traction system of claim 6 further comprising conveyor drum around which one of said at least one layers passes.

12. A traction system according to claim 6, wherein the radiolucent layer has variable elasticity, and wherein the puller exerts tension on the layer so as to effect variable movement of different regions of the layer.

13. A method of moving a tissue relative to at least one surface of a tissue imaging device comprising the steps of:
    positioning at least one layer of radiolucent material between at least one surface of said tissue and said at least one surface of said tissue imaging device, said radiolucent material being capable of movement relative to said at least one surface of said tissue imaging device;
    moving said at least one layer of radiolucent material relative to said at least one surface of said tissue imaging device such that at least a portion of said tissue also moves relative to said at least one surface of said tissue imaging device in the direction of motion of said at least one layer of radiolucent material so as to effect at least one of (a) pulling the tissue into the imaging device without substantially moving other portions of a patient's body to which the tissue is attached, and (b) shearing of the tissue.

14. The method of claim 13 wherein said tissue imaging device comprises a tissue compression system; said positioning step comprises positioning at least one layer of radiolucent material between at least one surface of said tissue and at least one surface of said tissue compression system, said radiolucent material being capable of movement relative to said at least one surface of said tissue compression system; and said moving step comprises moving said at least one layer of radiolucent material relative to said at least one surface of said tissue compression system in the direction of motion of said at least one layer of radiolucent material.

15. An imaging detection system comprising:
    a detector apparatus in operational engagement with at least one layer of radiolucent material, said at least one layer being dimensioned and constructed such that said layer can pass between tissue and a surface of said detector apparatus, said material having sufficient tensile strength that said layer can slide without tearing against said surface of said detector apparatus when tension is exerted on said layer, said sliding resulting in movement of at least a portion of said tissue relative to said surfaces of said detector apparatus, so as to effect at least one of (a) pulling the tissue into the imaging device without substantially moving other portions of a patient's body to which the tissue is attached, and (b) shearing of the tissue.

16. The imaging detection system of claim 15, further comprising a conveyor drum around which one of said at least one layer passes and with which said one of said at least one layer is operationally engaged to form a conveyor.

17. The imaging detection system of claim 15, wherein said detector apparatus comprises a support plate and wherein said surface of said detector apparatus comprises at least a portion of a surface of said support plate.

18. An imaging detection system according to claim 15, wherein the radiolucent layer has variable elasticity.

19. A layer of radiolucent material according to claim 18, wherein the layer is of variable thickness, having thinner portions that are more elastic and thicker portions that are less elastic.

20. A method of shearing tissue disposed between a compression plate and a support plate of a tissue imaging device comprising laterally translating either or both of said compression plate and said support plate relative to each other.

21. A method of shearing tissue disposed between a compression plate and a support plate of a tissue imaging device comprising twisting either or both of said compression plate and said support plate relative to each other.

22. A mammography device comprising:
    a compression plate and a support plate defining a compression/imaging space therebetween;
    at least one layer of radiolucent material dimensioned and constructed such that said at least one layer can pass between surfaces of either or both of said compression plate and said support plate and a breast inserted within said compression/imaging space, said material having sufficient tensile strength that said at least one layer can slide without tearing against said surfaces when tension is exerted on said layer, said sliding resulting in movement of said breast relative to said surfaces; and
    at least one puller capable of exerting tension on said at least one layer, said mammography device being arranged and constructed such that tension exerted by said at least one puller on said at least one layer results in sliding of said at least one layer against said surfaces such that said tissue moves relative to said surfaces.

23. The mammography device of claim 22, wherein either or both of said compression plate and said support plate are capable of lateral translation with respect to the other said plate, said lateral translation resulting in shearing of tissue disposed within said compression/imaging space between said compression plate and said support plate.

24. The mammography device of claim 22, wherein either or both of said compression plate and said support plate are capable of twisting with respect to the other said plate, said twisting resulting in shearing of tissue disposed within said compression/imaging space between said compression plate and said support plate.

25. The mammography device of claim 22, wherein either or both of said compression plate and said support plate are capable of both lateral translation and twisting with respect to the other said plate.

26. A compression element for a tissue imaging device comprising a compression plate in operational engagement with at least one layer of radiolucent material, said at least one layer being dimensioned and constructed such that said at least one layer can pass between tissue and a surface of said compression plate, said material having sufficient tensile strength that said layer can slide without tearing against said surface of said compression plate when tension is exerted on said layer, said sliding resulting in movement of said tissue relative to said surface of said compression plate.

27. The compression element of claim 26, further comprising a conveyor drum around which one of said at least one layers passes and with which said one of said at least one layers is operationally engaged to form a conveyor.

28. The compression element of claim 27 further comprising a support plate spaced apart from said compression plate, said compression plate and said support plate defining a compression space therebetween within which tissue can be compressed by movement of at least one said plate relative to the other said plate.

29. A layer of radiolucent material dimensioned and constructed such that said layer can pass between tissue disposed within a tissue imaging device and a surface of said tissue imaging device, said material having sufficient tensile strength that said layer can slide without tearing against said surface of said tissue imaging device when tension is exerted on said layer, said sliding resulting in movement of at least a portion of said tissue relative to said surface of said tissue imaging device so as to effect at least one of (a) pulling the tissue into the imaging device without substantially moving other portions of a patient's body to which the tissue is attached, and (b) shearing of the tissue.

30. A layer of radiolucent material according to claim 29, wherein the layer has variable elasticity.

31. A layer of radiolucent material according to claim 30, wherein the layer is of variable thickness, having thinner portions that are more elastic and thicker portions that are less elastic.

32. A mammography imaging device comprising:

a compression plate and a support plate defining a compression/imaging space therebetween;

at least one layer of radiolucent material dimensioned and constructed such that said at least one layer can pass between surfaces of either or both of said compression plate and said support plate and a breast inserted within said compression/imaging space, said material having sufficient tensile strength that said at least one layer can slide without tearing against said surfaces when tension is exerted on said layer, and at least one puller capable of exerting tension on said at least one layer so as to slide said at least one layer against said surfaces such that said breast moves relative to said surfaces so as to effect at least one of (a) pulling of the breast into the imaging device without substantially moving other portions of a patient's body to which the tissue is attached, and (b) shearing of the breast.

* * * * *